United States Patent [19]

Coffen

[11] 4,208,535

[45] Jun. 17, 1980

[54] NOVEL 4-PHENOXY-5-SULFAMYLBENZOIC ACID

[75] Inventor: David L. Coffen, Glen Ridge, N.J.

[73] Assignee: Hoffmann-La Roche Inc., Nutley, N.J.

[21] Appl. No.: 925,004

[22] Filed: Jul. 14, 1978

Related U.S. Application Data

[60] Division of Ser. No. 737,630, Nov. 1, 1976, Pat. No. 4,118,587, which is a continuation-in-part of Ser. No. 668,758, Mar. 22, 1976, abandoned.

[51] Int. Cl.$^2$ .................. C07C 143/78; A61K 31/195
[52] U.S. Cl. ..................................... 562/430; 424/317
[58] Field of Search .......................... 562/430

[56] References Cited

U.S. PATENT DOCUMENTS

| | | | |
|---|---|---|---|
| 3,875,150 | 4/1975 | Feit et al. | 562/430 |
| 3,971,819 | 7/1976 | Feit | 562/430 |
| 3,982,018 | 9/1976 | Werner | 562/430 |
| 3,991,097 | 11/1976 | Bormann et al. | 562/430 |

Primary Examiner—Alton D. Rollins
Assistant Examiner—M. C. Eakin
Attorney, Agent, or Firm—Jon S. Saxe; Bernard S. Leon; William H. Epstein

[57] ABSTRACT

Novel 3-(butylamino) or (1-pyrrolidinyl)-4-phenoxy-5-sulfamylbenzoic acid derivatives where the butyl group contains either a double bond or a hydroxy, ketone, acid or ester functional group or groups, said compounds being useful as diuretics.

2 Claims, No Drawings

NOVEL 4-PHENOXY-5-SULFAMYLBENZOIC ACID

CROSS REFERENCE TO RELATED APPLICATIONS

This is a division, of application Ser. No. 737,630 filed Nov. 1, 1976, now U.S. Pat. No. 4,118,587, which in turn is a continuation-in-part of Ser. No. 668,758 filed Mar. 22, 1976, now abandoned.

SUMMARY OF INVENTION

In accordance with this invention, it has been discovered that compounds of the formula:

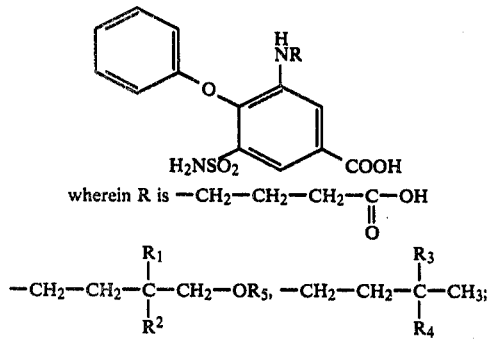

wherein R is $-CH_2-CH_2-CH_2-\underset{\underset{O}{\|}}{C}-OH$ $-CH_2-CH_2-\underset{R_2}{\overset{R_1}{C}}-CH_2-OR_5$, $-CH_2-CH_2-\underset{R_4}{\overset{R_3}{C}}-CH_3$;

$-CH_2-CH=CH-CH_3$ or $-CH_2-CH_2-CH=CH_2$; $R_1$ is individually hydrogen; $R_2$ is individually hydrogen or hydroxy; or taken together with $R_1$ is oxo; $R_3$ individually is hydroxy; $R_4$ is hydrogen or taken together with $R_3$ is oxo; and $R_5$ is lower alkanoyl or hydrogen; and;

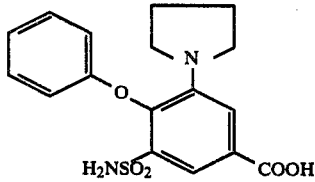

and pharmaceutically acceptable salts thereof; are useful as diuretics.

The compounds of formulae I and I-A can be prepared from a compound of the formula

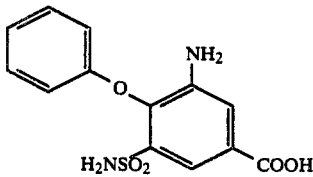

DETAILED DESCRIPTION

As used herein, the term halogen includes all four halogens which are chlorine, bromine, fluorine or iodine with chlorine being preferred. As used in this disclosure, the term "lower alkyl" comprehends both straight and branched chain carbon-hydrogen radicals containing from 1 to 7 carbon atoms, preferable 1 to 4 carbon atoms such as methyl, ethyl, propyl, isopropyl, butyl and the like. The term "lower alkanoyl" as used herein comprehends an acyl moiety of from 2 to 7 carbon atoms, preferably from 2 to 4 carbon atoms, such as acetyl, propionyl, butryl and the like. The term lower alkenyl designates alkenyl groups containing from 2 to 7 carbon atoms. Among the preferred alkenyl groups are vinyl, $-CH_2-CH=CH-CH_3$ or $-CH_2-CH_2-CH=CH_2$.

The compounds of formulae I and I-A as well as their pharmaceutically acceptable salts are diuretic and saluretic agents which can be used in the treatment of conditions associated with electrolyte and fluid retention and hypertension. When administered in therapeutic dosages, in conventional vehicles, the instant products effectively reduce the amount of sodium, potassium and chloride ions in the body, lower dangerous excesses of fluid levels to acceptable limits and, in general, alleviate conditions usually associated with edema.

The diuretic and saluretic properties of the compounds of formulae I and I-A and the salts thereof can be demonstrated by the following procedure.

Renal clearance studies were performed on fasted female beagle dogs (8–11 kg) anesthetized intravenously with pentobarbital sodium (30 mg/kg). After performing a tracheotomy the left jugular vein and right carotid artery were cannulated to facilitate the infusion of fluid and recording of blood pressure, respectively. To estimate the glomerular filtration rate (GFR), inulin was administered as a prime injection (35 mg/kg i.v.) and as a continuous infusion (1.1 mg/kg/min.) in saline (154 mM) at a rate of 0.5 ml/kg/min. To estimate the effective renal plasma flow (ERPF), para-aminohippuric acid (PAH) was given as a prime injection (3.5 mg/kg i.v.) and as a continuous infusion (400 mg/L) along with inulin. Following a midline incision each ureter was isolated and cannulated with polyethylene tubing. Urine collection from both kidneys was pooled and measured in graduated cylinders every 10–15 minutes. Blood samples were obtained at the midpoint of each urine collection from a catheterized femoral artery. Following one hour of equilibration in which 2 or 3 control urine samples were collected, compound of formulae I and I-A was intravenously administered as a bolus injection. No more than two compounds in saline (1:154 mM) were administered to the same dog. In addition, the doses as well as the compounds were randomized for each animal. In some experiments, labeled $^3$H-Inulin (2.5 μc/kg; 2.5 μc/kg/hr) and $^{14}$C-PAH (1 μc/kg; 1 μc/kg/hr) were used to estimate GFR and ERPF. Systemic blood pressure was measured from a carotid artery.

The effectiveness of the compounds of formulae I and I-A as saluretic and diuretic agents can be seen from the results obtained when the following compounds were administered by the above procedure.

A=N-(2-phenoxy-3-sulfamyl-3-carboxyphenyl)-γ-aminobutyric acid;

B=3-(δ-hydroxybutylamino)-4-phenoxy-5-sulfamylbenzoic acid;

C=3-(1-pyrrolidinyl)-4-phenoxy-5-sulfamylbenzoic acid;

D=3-(γ-oxobutylamino)-4-phenoxy-5-sulfamylbenzoic acid;

E=3-(γ-hydroxybutylamino)-4-phenoxy-5-sulfamylbenzoic acid.

F=3(2-butenylamino)-4-phenoxy-4-sulfamylbenzoic acid.

In the tables, N is the number of dogs utilized per test dose.

TABLE I

Effect of Compounds C, D, E and F on Electrolyte Excretion in the Anesthetized Dog ELECTROLYTE EXCRETION ($\mu$Eq/min.)

| Com-pound | Dose (mg/kg) | N | $U_{Na}V$ Pre | Post | Δ | $U_{Cl}V$ Pre | Post | Δ | $U_KV$ Pre | Post | Δ |
|---|---|---|---|---|---|---|---|---|---|---|---|
| C | .001 |   | 391 ± 88 | 413 ± 49 | 20 ± 52 | 459 ± 86 | 507 ± 48 | 47 ± 62 | 29 ± 3 | 33 ± 0 | 4 ± 4 |
|   | .010 | 3 | 350 ± 49 | 476 ± 106 | 126 ± 61 | 420 ± 54 | 605 ± 108 | 185 ± 55 | 31 ± 4 | 37 ± 7 | 6 ± 4 |
|   | .100 |   | 253 ± 35 | 740 ± 74 | 487 ± 104 | 313 ± 52 | 1002 ± 89 | 689 ± 134 | 23 ± 2 | 44 ± 4 | 22 ± 4 |
|   | .001 |   | 531 ± 42 | 546 ± 74 | 15 ± 61 | 679 ± 46 | 661 ± 97 | 18 ± 63 | 59 ± 7 | 57 ± 11 | 1 ± 5 |
| D | .010 | 3 | 437 ± 115 | 650 ± 114 | 213 ± 114 | 519 ± 149 | 828 ± 159 | 304 ± 131 | 36 ± 7 | 47 ± 13 | 11 ± 8 |
|   | .100 |   | 530 ± 28 | 1295 ± 61 | 765 ± 72 | 686 ± 47 | 1697 ± 54 | 1011 ± 54 | 58 ± 7 | 96 ± 2 | 38 ± 8 |
|   | .010 |   | 470 ± 138 | 498 ± 155 | 28 ± 44 | 567 ± 182 | 594 ± 202 | 27 ± 56 | 38 ± 14 | 38 ± 14 | 0 ± 2 |
| E | .100 | 3 | 473 ± 120 | 572 ± 129 | 99 ± 27 | 546 ± 121 | 731 ± 174 | 185 ± 56 | 37 ± 13 | 49 ± 16 | 13 ± 3 |
|   | 1.00 |   | 323 ± 36 | 684 ± 47 | 378 ± 15 | 364 ± 31 | 851 ± 43 | 487 ± 18 | 29 ± 2 | 52 ± 3 | 23 ± 1 |
|   | .001 |   | 451 ± 115 | 640 ± 108 | 155 ± 24 | 564 ± 173 | 804 ± 136 | 240 ± 40 | 38 ± 13 | 54 ± 6 | 17 ± 7 |
| F | .100 | 3 | 303 ± 57 | 912 ± 121 | 436 ± 45 | 385 ± 80 | 1210 ± 126 | 825 ± 164 | 33 ± 3 | 74 ± 10 | 41 ± 12 |
|   | 1.000 |   | 202 ± 76 | 443 ± 47 | 241 ± 88 | 242 ± 108 | 613 ± 70 | 371 ± 123 | 20 ± 5 | 40 ± 4 | 20 ± 5 |

TABLE II

Effect of Compound C, D and E and F on Renal Function in the Anesthetized Dog

RENAL FUNCTION (ml/min.)

| Com-pound | Dose (mg/kg) | N | Urine Volume Pre | Post | Δ | GFR Pre | Post | Δ | ERPF Pre | Post | Δ |
|---|---|---|---|---|---|---|---|---|---|---|---|
|   | .001 |   | 2.75 ± 0.49 | 2.80 ± 0.25 | 0.05 ± 0.46 | 44 ± 8 | 45 ± 6 | 0 ± 3 | 136 ± 27 | 140 ± 34 | 4 ± 8 |
| C | .010 | 3 | 2.42 ± 0.26 | 3.55 ± 0.73 | 1.13 ± 0.47 | 43 ± 7 | 39 ± 5 | −4 ± 3 | 142 ± 51 | 116 ± 31 | −26 ± 20 |
|   | .100 |   | 1.82 ± 0.28 | 6.25 ± 0.53 | 4.43 ± 0.74* | 38 ± 2 | 35 ± 4 | −3 ± 2 | 92 ± 15 | 100 ± 26 | 8 ± 12 |
|   | .001 |   | 4.80 ± 0.60 | 4.67 ± 0.89 | −.13 ± 0.36 | 48 ± 1 | 46 ± 3 | −2 ± 2 | 162 ± 19 | 152 ± 18 | −10 ± 2 |
| D | .010 | 3 | 3.20 ± 0.73 | 5.15 ± 1.11 | 1.95 ± 0.93 | 49 ± 6 | 50 ± 5 | 1 ± 3 | 198 ± 64 | 207 ± 50 | 9 ± 26 |
|   | .100 |   | 4.80 ± 0.36 | 10.10 ± 0.60 | 5.3 ± 0.96* | 46 ± 4 | 44 ± 4 | −2 ± 1 | 172 ± 33 | 191 ± 35 | 19 ± 3 |
|   | 0.10 |   | 3.12 ± 1.45 | 3.07 ± 1.43 | −.05 ± 0.28 | 49 ± 13 | 51 ± 12 | 2 ± 2 | 126 ± 38 | 132 ± 32 | 6 ± 7 |
| E | .100 | 3 | 3.07 ± 1.17 | 3.95 ± 1.30 | 0.88 ± 0.16* | 46 ± 11 | 49 ± 11 | 2 ± 0 | 127 ± 30 | 147 ± 26 | 20 ± 8 |
|   | 1.00 |   | 2.27 ± 0.65 | 5.13 ± 0.56 | 2.68 ± 0.11* | 47 ± 11 | 43 ± 9 | −4 ± 2 | 110 ± 12 | 122 ± 13 | 12 ± 6 |
|   | .001 | 3 | 3.07 ± .89 | 4.12 ± .72 | 1.05 ± 18 | 39 ± 5 | 42 ± 5 | 2 ± 1 |   |   |   |
| F | .100 | 5 | 2.25 ± .49 | 8.23 ± 1.07 | 6.00 ± 1.3 | 42 ± 2 | 43 ± 2 | 1 ± 3 |   |   |   |
|   | 1.000 | 4 | 1.63 ± .66 | 4.13 ± .39 | 2.50 ± .81 | 32 ± 4 | 27 ± 2 | −5 ± 4 |   |   |   |

*$p < .05$

TABLE III

Effect of Compounds A and B on Renal Function and Electrolyte Excretion in the Anesthetized Dog

| | | Renal Function | | | | Electrolyte Excretion | | | | | |
|---|---|---|---|---|---|---|---|---|---|---|---|
| | | Vol.[a] | | G.F.R.[b] | | Na⁺ | | K | | Cl⁻ | |
| | Dose | ml/min | | | | $\mu$Eq/min | | | | | |
| Compound | mg/kg | Pre | Post | Pre | Post | Pre | Post | Pre | Post | Pre | Post |
| A | 0.1 | 1.50 | 1.75 | 37 | 37 | 297 | 368 | 9 | 12 | 326 | 380 |
|   | 1.0 | 1.10 | 3.60 | 36 | 33 | 223 | 677 | 11 | 55 | 273 | 806 |
| B | 0.01 | 3.40 | 4.25 | 48 | 44 | 432 | 531 | 45 | 51 | 469 | 599 |
|   | 0.10 | 2.60 | 6.00 | 38 | 34 | 346 | 756 | 37 | 64 | 361 | 906 |
|   | 1.00 | 2.90 | 6.75 | 38 | 29 | 351 | 817 | 37 | 74 | 392 | 986 |

[a]Vol. = Urine Volume
[b]GFR = Glomerular Filtration Rate

The compounds of formulae I and IA as well as their pharmaceutically acceptable salts, can be used by the pharmaceutical arts in a variety of pharmaceutical preparations. In these preparations, the new compounds are administerable in the form of tablets, pills, powders, capsules, injectables, solutions, suppositories, emulsions, dispersions, and in other suitable forms. The pharmaceutical preparations which contain the compound of formulae I and IA as well as salts thereof, are conveniently admixed with a non-toxic pharmaceutical organic carrier or a non-toxic pharmaceutical inorganic carrier. Typical of pharmaceutically acceptable carriers are, for example, water, gelatin lactose, starches, magnesium stearate, talc, vegetable oils, polystyrene, glycols, petroleum jelly and other conventionally employed pharmaceutically acceptable carriers. The pharmaceutical preparations may also contain non-toxic auxiliary substances such as emulsifying, preserving and wetting agents and the like, as for example, sorbitan monolaurate, triethanol amine oleate, polyoxyethylene sorbitan, dioctyl sodium sulfosuccinate and the like.

The daily dose administered for the compounds will of course vary with the particular novel compounds employed because of the varying potency of the compounds, the chosen route of administration and the size of the recipient. The dosage administered is not subject to definite bounds but it will usually be in effective amounts of the pharmacologically function of the compound. Representative of a typical method for administering the compounds of formulae I and IA as well as salts thereof, is by oral type administration. By this route, the compounds of formulae I and IA and their salts can be administered orally at the rate of 0.01 to 0.5 mg. per day per kilogram of body weight.

The compounds of Formulae I and IA form salts with acids and bases. The bases are preferably those of therapeutically useful inorganic or organic bases, primarily the alkali metal, alkaline earth metal, e.g. sodium, potassium, magnesium or calcium salts, or ammonium salts from ammonia or amines, such as those of mono-, di- or tri-lower alkylamines, or tertiary nitrogen bases, such as pyridine, collidine or lutidine. Resulting compounds that contain basic groups, e.g. amino groups, may also form acid addition salts, preferably such of therapeutically useful inorganic or organic acids, such as strong metalloidic acids, for example hydrohalic, e.g. hydrochloric or hydrobromic acid, sulfuric, phosphoric, nitric or perchloric acid; strong organic acids e.g. methane or toluene sulfonic acids.

The compounds of formula I where R is

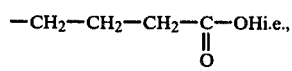

a compound of the formula:

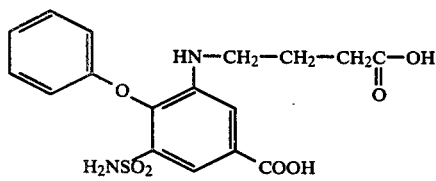

III-A and where R is —$CH_2$—$CH_2$—$CH_2$—$CH_2OH$ i.e.,

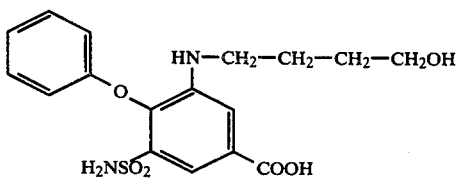

III-B can be prepared from the compound of formula II via the following intermediates.

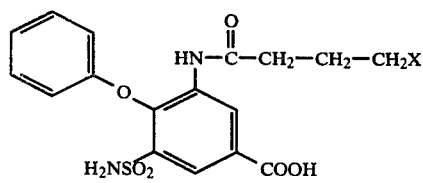

V

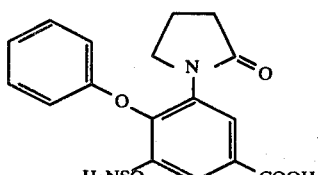

VI

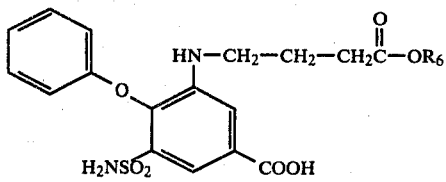

VII

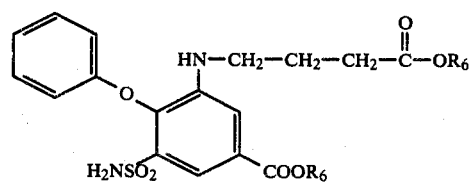

VIII where $R_6$ is lower alkyl or lower alkenyl and X is halo.

In accordance with this invention, the compound of formula II is reacted with a compound of this formula

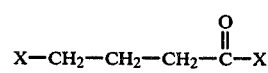

where X is halo to produce a compound of the formula V. The reaction is generally carried out in an ether solvent at reflux. Any conventional ether solvent can be utilized to carry out this reaction. Among the preferred ether solvents are tetrahydrofuran and dioxane.

In the next step, the compound of formula V is converted to the compound of formula III-A by treating the compound of formula V with a base in a polar solvent, i.e. water, dimethyl formamide, etc. Any conventional polar solvent can be utilized with water being preferred. Generally, any strong base such as alkali metal lower alkoxide, an alkali metal hydroxide preferably sodium hydroxide or potassium hydroxide can be utilized. In carrying out this reaction, the base is generally present in an amount of from about 2 to 50% by weight of the aqueous solution with amounts of from about 15 to 40% being preferred. This reaction is preferably carried out at elevated temperatures, i.e. temperatures of from about 40° C. and above. Generally this reaction is carried out at reflux temperature. When an organic polar solvent is utilized, the base must be an inorganic base such as an alkali metal or alkaline earth metal hydroxide. However, when water is utilized, any strong organic or inorganic base can be utilized.

On the other hand, the compound of formula III-A can be prepared from the compound of formula V via an intermediate of the formula VI. In this conversion, the compound of formula V is cyclized to the compound of formula VI by treating the compound of formula V with a weak base in an inert organic solvent, preferably and ether solvent. In carrying out this reaction, any organic solvent can be utilized with tetrahydrofuran and dioxane being preferred. Among the preferred bases are the weak, inorganic bases such as the alkali metal carbonates with potassium carbonate being preferred. Generally, this reaction is carried out at reflux. The compound of formula VI is converted to the compound of formula III-A by treating the compound of formula VI with a strong base in an aqueous medium utilizing the same conditions described in connection with the conversion of a compound of formula V to a compound of formula III-A.

In accordance with one embodiment of this invention, the compound of formula III-A is converted to the compound of formula III-B via the intermediate of the compound of the formula VII. The compound of the formula III-A is converted to the compound of formula VII by monoesterification with a lower alkanol or lower alkenyl alcohol. Any conventional method of monoesterifying the compound of formula VII can be utilized to affect this conversion. In accordance with the preferred embodiment of this invention, the compound of formula III-B is reacted with a lower alkanol or a lower alkenyl alcohol in the presence of a mineral acid. Generally, this reaction is carried out by utilizing the lower alkanol or the lower alkenyl alcohol as the solvent. In this reaction, any conventional mineral acid such as sulfuric acid can be utilized. Furthermore, this reaction is carried out at a temperature of from 40° C. to 70° C. for a period of from 2 to 6 hours. Generally, it is preferred to utilize a temperature of from 55°–65° C. for a period of from 2 to 4 hours.

The compound of formula VII is converted to the compound of formula III-B by selectively reducing the compound of the formula VII. This selective reduction is carried out by treating the compound of formula VII with any conventional borohydride reducing agent. Any conventional borohydride reducing agent can be utilized to carry out this conversion. Among the preferred borohydrides are included alkali metal borohydrides with sodium borohydride being preferred. This reaction is generally carried out in an ether solvent. Any conventional organic ether solvent such as the solvents mentioned herein before can be utilized. The preferred solvent for use in this reaction is tetrahydrofuran. In carrying out this reaction, temperature and pressure are not critical and this reaction can be carried out at room temperature. If desired, elevated or reduced temperatures can be utilized. Generally, it is preferred to carry out this reaction at temperatures of from 10° C. to 80° C. with room temperature being preferred. Where tetrahydrofuran is the solvent, it is preferred to utilize the reflux temperature of the reaction medium.

On the other hand, the compound of formula III-A can be converted to the compound of formula III-B via the intermediate of the formula VIII. The intermediate of the formula VIII is formed from the compound of formula III-A by esterification so that both acid groups contained within the compound of formula III-A are esterified. Any conventional means of double esterification can be utilized to carry out this procedure. In accordance with the preferred embodiment, this procedure is carried out by treating the compound of formula III-A with a lower alkanol or lower alkenyl alcohol in the presence of an acid catalyst. Generally, the acid catalyst is a strong mineral acid such as sulfuric acid. The lower alkanol or the lower alkenyl alcohols form the reaction medium in this reaction. Generally, this reaction is carried out by refluxing the compound of formula III-A in the reaction medium containing the strong mineral acid catalyst. In this manner, both the free carboxyl groups in the compound of formula III-A are esterified.

The compound of formula VIII can be converted to the compound of formula III-B via an intermediate of the formula:

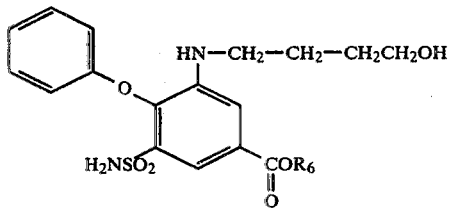

VIII-A where $R_6$ is lower alkyl.

The compound of formula VIII is converted to the compound of formula VIII-A by treating the compound of formula VIII with an aluminum hydride reducing agent. Any conventional aluminum hydride reducing agent can be utilized to carry out this reduction. Among the preferred reducing agents are the alkali and alkyl aluminum hydride reducing agents such as lithium aluminum hydride, diisobutyl aluminum hydride, sodium bis-[2-methoxyethoxy]-aluminum hydride. The reduction with aluminum hydride agent is carried out in an inert organic solvent medium. Any conventional inert organic solvent medium can be utilized to carry out this reaction. Among the preferred inert organic solvents are tetrahydrofuran, dioxane, etc. In carrying out this reaction, generally one half an equivalent of the aluminum hydride reducing agent is utilized per equivalent of the compound of formula VIII. In carrying out this reaction, temperature and pressure are not critical and this reaction is generally carried out at room temperature and atmospheric pressure. On the other hand, elevated or reduced temperatures can be utilized. Generally, temperatures of from 0° C. to 35° C. are utilized in carrying out this reduction.

The compound of formula VIII-A is converted to the compound of formula III-B by hydrolysis. Any conventional method of alkaline hydrolysis can be utilized to carry out this conversion. Generally, it is preferred to treat this compound with an aqueous solution containing an inorganic alkaline metal hydroxide such as sodium hydroxide or potassium hydroxide. In carrying out this reaction, temperature and pressure are not critical and this reaction can be carried out at room temperature. If desired, higher or lower temperatures can be utilized.

In accordance with this invention, the compound of formula I where R is

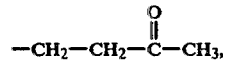

i.e., a compound of the formula:

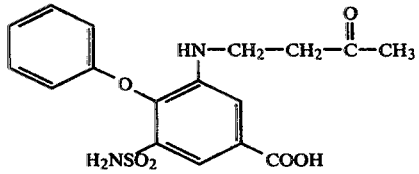

III-C is prepared from a compound of the formula II by reacting this compound with a compound of formula

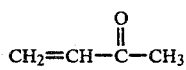

This reaction is carried out in the presence of an organic polar solvent. Any conventional inert organic polar solvent which include lower alkanol solvents such as ethanol, butanol, etc; ether solvents such as dioxane, tetrahydrofuran, etc. can be utilized. This reaction is generally carried out at the reflux temperature of the reaction medium.

The compound of formula III-C can be converted to the compound of formula I where R is

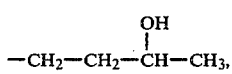

i.e., a compound of the formula:

III-D
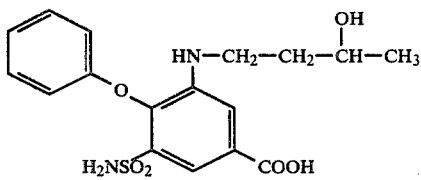

by reduction with an alkali metal borohydride reducing agent. This reduction is carried out in the same manner as described in connection with the conversion of a compound of formula VII to a compound of formula III-B.

In accordance with this invention, the compound of formula I where R is —CH$_2$—CH$_2$CH=CH$_2$, i.e., a compound of the formula:

III-E
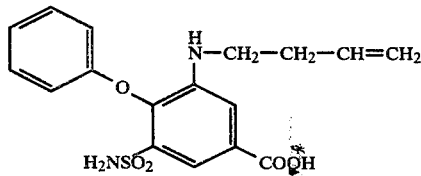

is prepared from a compound of formula II by reacting the compound of formula II with

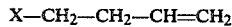X-A

where X is as above in the presence of a lower alkanol or lower alkenyl alcohol as a solvent to form a compound of the formula:

XII
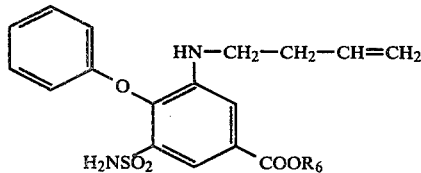

wherein R$_6$ is as above which is then hydrolyzed to produce the compound of formula III-E.

The reaction of the compound of formula X-A with a compound of formula II takes place in the presence of a strong organic acid catalyst. Any conventional strong organic acid catalyst can be used to carry out this reaction with p-toluene sulfonic acid being preferred. This reaction is carried out at the reflux temperature of the reaction medium.

Hydrolysis of the compound of formula XII to produce a compound of formula III-E is carried out by treating the compound of formula XII with a base in a lower alkanol solvent at a temperature of from 10° C. to 30° C. with room temperature being preferred. Any conventional lower alkanol such as methanol, ethanol, etc., can be used as the solvent medium. Any conventional inorganic alkali metal base such as sodium or potassium hydroxide can be used in this reaction.

The compound of formula I-A can be prepared from the compound of formula II via the following intermediates.

XV
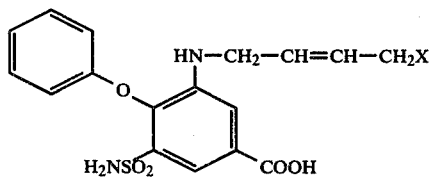

XVI
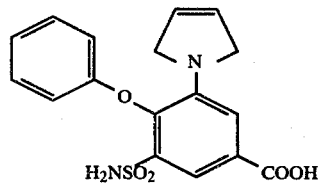

In preparing the compound of formula XV, the compound of formula II is reacted with

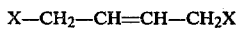 XVII where X is as above.

The compound of formula II is reacted with the compound of formula XVII to produce the compound of formula XV in a organic ether or halogenated hydrocarbon solvent medium. In carrying out this reaction, any conventional organic ether or halogenated hydrocarbon solvent can be utilized with tetrahydrofuran and dioxane being preferred. Generally, this reaction is carried out at a temperature of from 60° C. to 120° C. with reflux temperatures being preferred.

The compound of formula XV is converted to the compound of formula XVI by treating the compound of formula XV with a lower alkanoic acid, preferably acetic acid. Generally, this reaction is carried out at a temperature of from 50° C. to 80° C. with temperatures of from about 60°–70° C. being preferred. The compound of formula XVI is converted to the compound of formula I-A by hydrogenation. Any conventional means of hydrogenation such as by treating the compound of formula XVI with hydrogen gas utilizing a conventional hydrogenation catalyst. Any conventional hydrogenation catalyst can be utilized to carry out this reaction. Among the preferred hydrogenation catalysts is included Rainey nickel. In carrying out this reaction, temperature and pressure are not critical and this reaction can be carried out at room temperature and atmospheric pressure.

The compound of formula II can be converted to the compound of formula I where R is

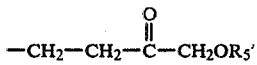

where R₅' is lower alkanoyl

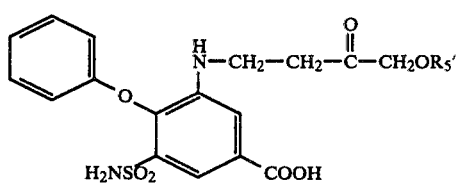

where R₅' is as above by reaction with a compound of the formula:

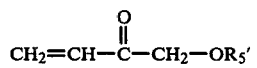

where R₅' is as above. This reaction is carried out in a organic polar solvent such as the polar solvents mentioned above. Any conventional polar solvent can be utilized to carry out this reaction. Generally this reaction is carried out at the reflux temperature of the reaction medium.

In accordance with this invention, the compound of formula III-F can be converted to the compound of formula I where R is

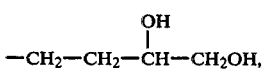

i.e., a compound of the formula:

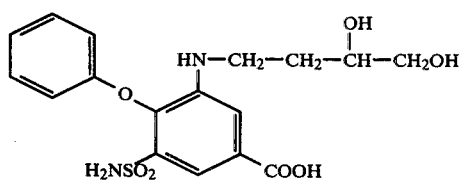

or a compound of the formula

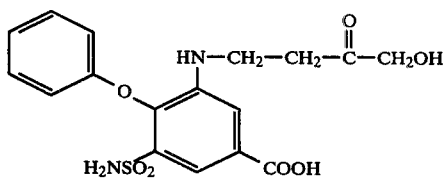

The compound of III-F is converted to the compound of III-G by reduction with a borohydride reducing agent. Any conventional borohydride reducing agent can be utilized to carry out this reaction. Among the preferred borohydride reducing agents are the alkali metal borohydrides such as sodium borohydride. Generally, this reaction is carried out in the presence of a lower alkanol solvent. Any conventional lower alkanol solvent can be utilized to carry out this reaction. In carrying out this reaction, temperature and pressure are not critical and this reaction can be carried out at room temperature and atmospheric pressure. If desired, higher or lower temperatures can be utilized. Generally, temperatures from 20°–50° C. are utilized, with room temperature being preferred.

The compound of formula III-F is converted to the compound of formula III-H by conventional hydrolysis. Any conventional method of hydrolyzing an ester group can be utilized to carry out this conversion. Generally, it is preferred to carry out this conversion by treating the compound of formula III-F with a aqueous alkali solution such as an aqueous solution containing sodium hydroxide.

The compounds of formula III-D and III-G contain asymmetric carbon atoms. The compounds of III-E and III-G which are useful as diuretics include the various mixtures of the optical antipodes including the racemic mixtures as well as the optical antipodes themselves. Both the compound of III-D and III-G can be resolved into their optical antipodes by any conventional means for resolving these compounds. Among the methods for resolving these compounds are to form salts thereof with optically active amines such as brucine, α-methylbenzylamine, p-nitro-α-methyl benzylamine, dehydroabietylamine, etc. The optically active antipodes are regenerated from the salts after separation by treatment with an aqueous solution containing a strong mineral acid such as hydrochloric acid.

The compound of formula I where R is —CH₂—CH=CH—CH₃, i.e. a compound of the formula

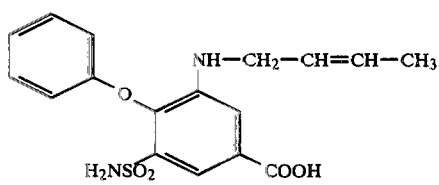

is prepared from a compound of formula III via an intermediate of the formula:

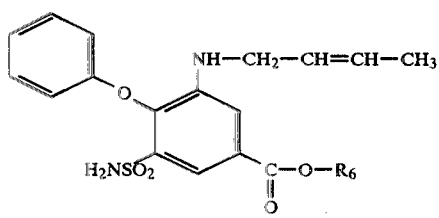

wherein R₆ is as above.

The compound of formula II is converted to the compound of formula XIX by reaction into a compound of the formula:

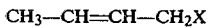

wherein X is as above. This reaction is carried out by reacting the compound of formula II with a compound of formula XX in a lower alkanol or lower alkenyl alcohol solvent. The lower alkanol or lower alkenyl alcohol solvent esterifies with the free acid group in the compound of formula II to form the R₆ substituent. In carrying out this reaction, temperatures of from 40° C. to 90° C. are generally utilized. The compound of formula XIX is converted to the compound of formula III-J by aqueous basic hydrolysis. Any conventional basic hydrolysis can be utilized in this conversion.

In accordance with another embodiment, the compound of formula III-B and III-G can be converted to the compound of formula I where R is

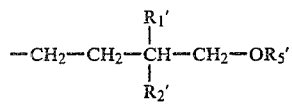

where $R_1'$ is hydrogen, $R_2'$ is hydrogen or hydroxy and $R_5'$ is as above by esterification with an organic acid or a reactive derivative thereof. Any conventional method of esterifying a primary alcohol with an organic acid can be utilized to carry out this reaction. Among the reactive acid derivatives that are preferred for utilization in accordance with this invention are the acid halides and acid anhydrides. Any of the conditions conventional in utilizing these derivatives can be utilized to carry out this reaction. Where R is

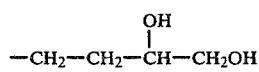

(the compound of formula III-G), the primary alcohol will esterify before the secondary alcohol. Therefore, the compound of formula I where R is

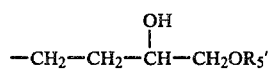

will be produced.

The following examples are illustrative but not limitative of the invention. All temperatures are in degrees Centigrade.

EXAMPLE 1

3-(γ-Chlorobutyrylamino)-4-phenoxy-5-sulfamylbenzoic acid

A solution of 3-amino-4-phenoxy-5-sulfamylbenzoic acid (10 g, 0.0325 mole) and 4-chlorobutyrylchloride (4.5 ml, 0.04 mole) in dioxane (100 ml) was heated under reflux for 4 hours. After cooling, ether (100 ml) was added and the precipitated product collected giving 11.3 g (84%) of colorless powder. A sample recrystallized from THF/CH$_2$Cl$_2$ gave 3-(γ-chlorobutyrylamino)-4-phenoxy-5-sulfamylbenzoic acid as colorless crystals with m.p. 243°–235°; ir (Nujol) 3300, 2600 (broad), 1700, 1600 and 1540 cm$^{-1}$; nmr (d$_6$-DMSO) 1.3–2.2 (m, 4H), 3.30 (t, J=6, CH$_2$), 3.5 (broad, NH), 6.6–7.7 (m, C$_6$H$_5$ and SO$_2$NH$_2$), 8.18 (d, J=2, CH), 8.27 (d, CH), and 9.38 ppm (s, COOH); mass spectrum m/e 36 and 38 (100%, HCl), 334 and 376 (no M$^+$ peak).

EXAMPLE 2

N-(2-Phenoxy-3-sulfamyl-5-carboxyphenyl)-γ-aminobutyric acid

The chlorobutyramide 3-(γ-chlorobutyrylamino)-4-phenoxy-5-sulfamylbenzoic acid (11.0 g) was added to a solution of KOH (40 g) in water 100 ml. The resulting solution was stirred and heated under reflux overnight. After cooling it was acidified with 3 N acqueous HCl, chilled by adding ice and the product collected, washed and air-dried. A recrystallization from aq. acetone gave 9.80 g (77% on two steps) of N-(2-phenoxy-3-sulfamyl-5-carboxyphenyl)-γ-aminobutyric acid as colorless crystals with m.p. 240°–241°; ir (Nujol) 3400, 3300, 2600 (broad), 1700, 1610, 1590, and 1550 cm$^{-1}$; nmr (CDCl$_3$/d$_6$-DMSO) 1.4–2.3 (m, 4H), 3.15 (m, 2H), 4.2 (broad, NH), 6.43 (s, SO$_2$NH$_2$), 6.65–7.4 (m, C$_6$H$_5$), 7.57 (d, J=2, CH), and 7.92 ppm (d, CH); mass spectrum m/e 283 (100%) and 394 (M$^+$).

EXAMPLE 3

3-(2-Oxo-1-pyrrolidinyl)-4-phenoxy-5-sulfamylbenzoic acid

The compound 3-(γ-chlorobutyrylamino)-4-phenoxy-5-sulfamylbenzoic acid (11.5 g) and anhydrous potassium carbonate (11.5 g) were slurried in dioxane (350 ml) and stirred under reflux overnight. The solvent was removed under reduced pressure and the residue taken up in a small volume of water. After acidification with 3 N acqueous HCl, the product separated as a gum. Methylene chloride was added and the mixture stirred for 1 hour. The product 3-(2-oxo-1-pyrrolidinyl)-4-phenoxy-5-sulfamylbenzoic acid, now in the form of a powder, was filtered, washed with water, and air-dried to give 7.5 g (61% on two steps). A sample was recrystallized from aq. dioxane to give colorless crystals with m.p. 282°–285°; ir (Nujol) 3400, 3250, 2600 (broad), 1735, 1660, 1600, and 1575 cm$^{-1}$; nmr (d$_6$-DMSO) 1.2–2.3 (m, 4H), 3.41 (t, J=6, 2H), 6.7–7.5 (m, C$_6$H$_5$), 7.65 (s, SO$_2$NH$_2$), 8.15 (d, J=2, CH), and 8.46 ppm (d, CH); mass spectrum m/e 283 (100%) and 376 (M$^+$).

EXAMPLE 4

N-(2-Phenoxy-3-sulfamyl-5-carboxyphenyl)-γ-aminobutyric acid diethyl ester

A solution of the diacid N-(2-phenoxy-3-sulfamyl-5-carboxyphenyl)-γ-aminobutyric acid (5 g) in ethanol (100 ml) was treated with conc. sulfuric acid (0.5 ml) and heated under reflux overnight. After evaporation of the ethanol under reduced pressure, the solid residue was triturated with water and made slightly basic with aq. Na$_2$CO$_3$. The solid was filtered, washed with water, partly air-dried, and dissolved in acetone. Some acetone insoluble material, probably the ester of pyrrolidinone 3-(2-oxo-1-pyrrolidinyl)-4-phenoxy-5-sulfamylbenzoic acid, was filtered out. The filtrate was concentrated under reduced pressure with gradual addition of water. The product N-(2-phenoxy-3-sulfamyl-5-carboxyphenyl)-γ-aminobutyric acid diethyl ester separated in colorless crystals, 4.8 g (84%), with m.p. 130°–132°; ir (Nujol) 3350, 3250, 1740, 1720, 1615, 1595, and 1550 cm$^{-1}$; nmr (CDCl$_3$) 1.0–2.4 (m, 10H), 3.17 (q, 2H, t after D$_2$O wash), 4.12 (q, 2H), 4.43 (q, 2H), 5.08 (s, SO$_2$NH$_2$), 6.8–7.5 (m, C$_6$H$_5$), 7.58 (d, J=2, 1H), and 7.98 ppm (d, 1H); mass spectrum m/e 349, 450 (100% M$^+$).

EXAMPLE 5

Ethyl N-(2-Phenoxy-3-sulfamyl-5-carboxyphenyl)-γ-aminobutyrate

A solution of the diacid N-(2-phenoxy-3-sulfamyl-5-carboxyphenyl)-γ-aminobutyric acid (1 g) in ethanol (25 ml) was treated with 6 drops of conc. aqueous sulfuric acid and the solution was heated to 60° C. for 3 hours. Tlc analysis showed that the reaction was complete. The solution was poured into water (250 ml) and stirred for 20 min. The product was collected, dried, and recrystallized from ether/pet. ether to give 750 mg (70%) of ethyl N-(2-phenoxy-3-sulfamyl-5-carboxyphenyl)-γ-aminobutyrate as colorless needles with m.p. 175°–177°; ir (Nujol) 3400, 3250, 1730, 1710, 1625, 1600, and 1525 cm$^{-1}$; nmr (CDCl$_3$/d$_6$-DMSO/D$_2$O-washed) 1.35 (t, 3H), 1.6–2.5 (m, 4H), 3.27 (t, 2H), 4.18 (q, 2H), 6.8–7.5 (m, 5H), 7.60 (d, J=2, 1H), and 8.00 ppm (d, 1H); mass spectrum m/e 422 (100%, M+).

EXAMPLE 6

3-(δ-Hydroxybutylamino)-4-phenoxy-5-sulfamylbenzoic acid (a) From the diester

A slurry of LiAlH$_4$ (800 mg) in THF (20 ml) was prepared and a filtered solution of N-(2-phenoxy-3-sulfamyl-5-carboxyphenyl)-γ-aminobutyric acid diethyl ester (2 g) in THF (20 ml) was added to this at room temp. The resulting mixture was stirred for 10 min; the lumps which formed were crushed. The mixture was quenched quickly with 3 N aqueous HCl and the pH of th resulting solution adjusted to ca. 4. The product mixture was extracted into ethyl acetate. Some starting material crystallized from an ether solution of the crude product mixture. Starting material was filtered off and the mixture in the filtrate separated on six preparative tlc plates (SiO$_2$). The starting material band and the band below it were collected. The ester-alcohol from the lower band was taken up in a solution of KOH (2 g) in methanol (20 ml) and kept overnight. The solution was diluted with water, made slightly acidic, and extracted with ethyl acetate. The residue from this extract was recrystallized from ethyl acetate/ether to give 120 mg (14% based on ca. 1 g of diester recovered) of 3-(δ-hydroxybutylamino)-4-phenoxy-5-sulfamylbenzoic acid as small, colorless needles with m.p. 205°–208°; ir 3500, 3200, 2600 (broad), 1690, 1615 and 1585 cm$^{-1}$; nmr (CDCl$_3$/-d$_6$-DMSO) 1.4 (m, 4H), 3.10 (m, 2H), 3.43 (t, 2H), 4.10 (broad, NH), 6.20 (s, SO$_2$NH$_2$), and 6.8–8.0 ppm (m, 7H, aromatic); mass spectrum m/e 321 (100%) and 380 (M+).

(b) From the monoester

A solution of the monoester ethyl N-(2-phenoxy-3-sulfamyl-5-carboxyphenyl)-γ-aminobutyrate (200 mg) in THF (15 ml) was treated with NaBH$_4$ (500 mg) and stirred at reflux for 3 days. Excess hydride was destroyed by adding 2% aq. HCl and the solution was partitioned between water and CH$_2$Cl$_2$. The organic layer was dried and evaporated. The solid residue was triturated with ether and filtered. The filtrate gave a second crop (15 mg). The product 3-(δ-hydroxybutylamino)-4-phenoxy-5-sulfamylbenzoic acid was thus obtained as 105 mg (58%) of a colorless solid and identified by comparison of ir spectra and by tlc.

EXAMPLE 7

3-(γ-Oxobutylamino)-4-phenoxy-5-sulfamylbenzoic acid

A mixture of 3-amino-4-phenoxy-5-sulfamylbenzoic acid (5 g) and methyl vinyl ketone (5 ml) in ethanol (100 ml) was stirred at reflux for 3 days. After cooling, the product 3-(γ-oxobutylamino)-4-phenoxy-5-sulfamylbenzoic acid was collected to give 5.05 g (82%) in two crops of colorless solid. An analytical sample from aq. acetone had m.p. 215°–215.5°; ir (Nujol) 3400, 3250, 1710, 1695, 1615, 1590, and 1570 cm$^{-1}$; nmr (CDCl$_3$/d$_6$-DMSO/D$_2$O-washed) 2.00 (s, CH$_3$), 2.60 (t, CH$_2$), 3.37 (t, CH$_2$), 6.8–7.4 (m, C$_6$H$_5$), 7.60 (d, J=2, CH), and 7.93 (d, CH); mass spectrum was of decomposition products, 308 (100%).

EXAMPLE 8

3-(γ-Hydroxybutylamino)-4-phenoxy-5-sulfamylbenzoic acid

A mixture of the ketone 3-(γ-oxobutylamino)-4-phenoxy-5-sulfamylbenzoic acid (3 g), sodium borohydride (1.6 g), ethanol (100 ml) and THF (100 ml) was stirred at room temp. for 1 hour. Excess hydride was destroyed by adding 2% aq. HCl and the solution was partitioned between aqueous base and CH$_2$Cl$_2$. The aqueous layer was acidified and extracted twice with CH$_2$Cl$_2$. The residue from the dried extracts was recrystallized from ethanol/CH$_2$Cl$_2$ to give 2.7 g (89%) of 3-(γ-hydroxybutylamino)-4-phenoxy-5-sulfamylbenzoic acid as colorless crystals with m.p. 245°–247°; ir (Nujol) 3340, 2600 (broad), 1685, 1605, 1580 and 1550 cm$^{-1}$; nmr (CDCl$_3$/d$_6$-DMSO/D$_2$O-washed) 1.07 (d, CH$_3$), 1.52 (q, CH$_2$), 3.20 (t, CH$_2$), 3.65 (m, CH), 6.8–7.4 (m, C$_6$H$_5$), 7.55 (d, J=2, CH), and 7.90 (d, CH); mass spectrum m/e 380 (100%, M+).

EXAMPLE 9

3-(4-Bromo-trans-2-butenylamino)-4-phenoxy-5-sulfamylbenzoic acid

A solution of 3-amino-4-phenoxy-5-sulfamylbenzoic acid (2 g) and 1,4-trans-dibromo-2-butene (3.2 g) in dioxame (35 ml) was heated to reflux overnight. The solvent was removed under reduced pressure and the dark, gummy residue was chromatographed on a silica gel column using chloroform/benzene/acetic acid/methanol (80:10:10:2.5) as the eluting solvent. The fractions containing the product were combined and concentrated leaving an acetic acid solution of it. This was diluted with water to give a cream colored powder which was filtered, dried and washed with pet. ether to remove unreacted dibromobutene. The resulting 3-(4-bromo-trans-2-butenylamino)-4-phenoxy-5-sulfamylbenzoic acid was an off-white solid 0.75 g (26%) with m.p. 191°–194°; ir (Nujol) 3350, 3200, 2600 (broad), 1690, 1605, 1585, and 1530 cm$^{-1}$; nmr (CDCl$_3$/d$_6$-DMSO) 3.7–4.5 (m, 5H incl. NH), 5.73 (t, 2H, vinyl), 6.27 (s, SO$_2$NH$_2$), 6.8–7.4 (m, C$_6$H$_5$), 7.57 (d, J=2, CH), and 8.03 ppm (d, CH); mass spectrum is of decomposition products.

EXAMPLE 10

N-(2-Phenoxy-3-sulfamyl-5-carboxyphenyl)-Δ$^3$-pyrroline

A solution of the bromobutenyl derivative 3-(4-bromo-trans-2-butenylamino)-4-phenoxy-5-sulfamylbenzoic acid (9.1 g) in acetic acid (60 ml) was heated to 60° overnight. The solution was then poured into a mixture of ice and water and stirred vigorously for ½ hr. The product was collected, washed with water and air-dried to give 7.25 g (97%) of N-(2-phenoxy-3-sulfamyl-5-carboxyphenyl)-Δ$^3$-pyrroline as a tan powder. A sample recrystallized from CH$_2$Cl$_2$/hexane had m.p. 227°–230°; ir 3400, 3250, 2600 (broad), 1690, 1590, and 1570 cm$^{-1}$; nmr (CDCl$_3$/d$_6$-DMSO/D$_2$O-washed) 4.25 (s, 4H), 5.80 (s, broad, 2H, vinyl), 6.7–7.5 (m, C$_6$H$_5$), 7.65 (d, J=2, CH), and 8.01 ppm (d, CH); mass spectrum m/e 279 (100%) and 360 (M+).

EXAMPLE 11

3-(1-Pyrrolidinyl)-4-phenoxy-5-sulfamylbenzoic acid

A solution of the N-(2-phenoxy-3-sulfamyl-5-carboxyphenyl)-Δ³-pyrroline (7.25 g) in methanol (150 ml) was shaken with 1 g of Raney nickel under 50 psi of hydrogen for 22 hours. The solution was then filtered, evaporated, and the residue was triturated with a little chloroform and filtered. Recrystallization from methanol/$CH_2Cl_2$ gave 6.9 g (95%) of 3-(1-pyrrolidinyl)-4-phenoxy-5-sulfamylbenzoic acid as colorless crystals with m.p. 214°–217°; ir (Nujol) 3350, 3250, 2600 (broad), 1690, 1610, 1590, and 1570 cm$^{-1}$; nmr ($CDCl_3$/$d_6$-DMSO/$D_2O$-washed), 1.79 (s, broad, 4H), 3.30 (s, broad, 4H), 6.7–8.1 (m, 7H, aromatic); mass spectrum m/e 252 (100%) and 362 (M+).

EXAMPLE 12

3-(But-3-enylamino)-4-phenoxy-5-sulfamylbenzoic acid

A solution of 3-amino-4-phenoxy-5-sulfamylbenzoic acid (7.5 g), 4-bromo-1-butene (12 ml), and p-toluenesulfonic acid (500 mg) in 3-buten-1-ol (35 ml) was heated under reflux for 6 days. Most of the solvent was recovered by distillation. The concentrated solution was diluted with pet. ether and stirred for ½ hour. The ester of the product was collected (3.9 g) and hydrolyzed in 10% by weight methanolic KOH at room temperature. A second crop of 4.0 g was a mixture of the esters of starting material and product. These were not separated. The 3.9 g crop afforded 3.1 g (35%) of 3-(but-3-enylamino)-4-phenoxy-5-sulfamylbenzoic acid which was clean by tlc. Recrystallization from ether/pet. ether gave colorless crystals. The analytical sample was sublimed in vacuum. The product had mp 228°–32° (dec); ir (Nujol) 3350, 3200, 2600 (broad), 1680, 1610, 1585, 1540 and 1515 cm$^{-1}$; nmr ($CDCl_3$/$d_6$-DMSO/$D_2O$-washed) 2.17 (q, 2H), 3.13 (t, 2H), 3.13 (t, 2H), 4.6–6.0 (m, 3H, vinyl), 6.8–7.5 (m, $C_6H_5$), 7.55 (d, J=2, CH), and 7.95 ppm (d, CH); mass spectrum m/e 321 (100%) and 363 (M+).

EXAMPLE 13

3-(γ-Oxo-δ-acetoxybutylamino)-4-phenoxy-5-sulfamylbenzoic acid

A solution of 3-amino-4-phenoxy-5-sulfamylbenzoic acid (5 g) in ethanol (100 ml) was prepared by heating. To this was added acetoxymethylvinyl ketone (5 ml) and the solution was heated at reflux for 14 hours. After cooling to room temperature, the product separated as a colorless solid. This was filtered and dried to give 6.45 g (91%) of 3-(γ-oxo-δ-acetoxybutylamino)-4-phenoxy-5-sulfamylbenzoic acid as colorless product which was pure by tlc. An analytical sample was recrystallized from aqueous acetone giving colorless needles with mp 190°–2°; ir (Nujol) 3600, 3400, 2700 (broad), 1755 (shoulder), 1740, 1700, 1620, 1600, and 1520 cm$^{-1}$; nmr ($CDCl_3$/$d_6$-DMSO/$D_2O$-washed) 2.13 (s, $CH_3$), 2.59 (t, J=6, $CH_2$), 3.43 (t, J=6, $CH_2$), 4.50 (s, $CH_2$), 6.8–7.4 (m, $C_6H_5$), 7.55 (d, J=2, 1H), and 7.92 ppm (d, J=2, 1H).

EXAMPLE 14

3-(γ,δ-Dihydroxybutylamino)-4-phenoxy-5-sulfamylbenzoic acid

A slurry of 3-(γ-oxo-δ-acetoxybutylamino)-4-phenoxy-5-sulfamylbenzoic acid (1.5 g) in ethanol (10 ml) was treated with sodium borohydride (0.5 g) and the mixture was heated on the steam bath with occasional swirling until a clear solution had formed. Water and aq. $Na_2CO_3$ were added and heating on the steam bath continued for about 10 min. The solution was cooled and carefully acidified with 3 N aqueous HCl. Some methanol was added and the solution was concentrated to ca. 20 ml under reduced pressure. Partial neutralization with aq. $Na_2CO_3$ caused the product to separate as a gum, which soon solidified. The product was filtered, washed with water, and air-dried to give 1.1 g (80%) of 3-(γ,δ-dihydroxybutylamino)-4-phenoxy-5-sulfamylbenzoic acid as a colorless powder. A sample was recrystallized from methanol/water to give needles with mp 235°–238°; ir (Nujol) 3500, 3400, 2700 (broad) 1710, 1625, 1600, and 1525 cm$^{-1}$; nmr ($d_6$-DMSO) 1.5 (m, broad, 2H), 3.0–3.5 (m, broad, 5 H), 5.13 (s, broad, NH), 6.7–7.3 (m, $C_6H_5$), 7.17 (s, $SO_2NH_2$), 7.31 (d, J=2, CH), and 7.66 ppm, d, J=2, CH); mass spectrum m/e 378, 396 (M+).

EXAMPLE 15

3-(2-Butenylamino)-4-phenoxy-4-sulfamylbenzoic acid

A mixture of 3-amino-4-phenoxy-5-sulfamylbenzoic acid (5.0 g) and crotyl bromide (15 ml) in ethanol (50 ml) was heated to 60° C. for three days. About half the solvent was then evaporated and the solution cooled. The ethyl ester of 3-(2-Butenylamino)-4-phenoxy-sulfamylbenzoic acid which precipitated was collected by filtration, washed with cold ethanol, and air dried.

Hydrolysis of the ester was accomplished by stirring in 1 N aqueous NaOH for 2 hours at room temperature. The solution was then acidified with 3 N aqueous HCl and the product extracted with diethyl ether. The extracts were dried and treated with charcoal. Evaporation of the solvent gave 3-(2-Butenylamino)-4-phenoxy-4-sulfamylbenzoic acid as a clean, colorless product (3.6 g). A microanalytical sample recrystallized from ethanol/chloroform had mp 239°–241° C.

EXAMPLE 16

| Item | TABLET FORMULATION: - (Wet Granulation) Ingredients | mg/tablet | mg/tablet |
|---|---|---|---|
| 1. | 3-(γ-oxobutylamino)-4-phenoxy-5-sulfamyl benzoic acid | 0.1 | 2.0 |
| 2. | Lactose | 152.9 | 253.0 |
| 3. | Modified starch | 25 | 55.0 |
| 4. | Pregelatinized starch | 20 | 35.0 |
| 5. | Distilled water q.s. | — | — |
| 6. | Magnesium stearate | 2 | 5.0 |
|  | Weight of tablet | 200 mg |  |

PROCEDURE:
(1) Mix Items 1–4 in a suitable mixer.
(2) Granulate with sufficient distilled water to proper consistency. Mill.
(3) Dry in a suitable oven.
(4) Mill and mix with magnesium stearate for 3 minutes.
(5) Compress on a suitable press equipped with appropriate punches.

EXAMPLE 17

| Item | CAPSULE FORMULATIONS: Ingredients | mg/tablet | mg/capsule |
|---|---|---|---|
| 1. | 3-(γ-oxobutylamino)-4-phenoxy-5-sulfamyl benzoic acid | 0.1 | 2.0 |
| 2. | Lactose | 103.9 | 375.5 |
| 3. | Starch | 30 | 45.0 |
| 4. | Talc | 15 | 25.0 |
| T | Aerosol OT | 1.0 | 2.5 |

-continued

CAPSULE FORMULATIONS:

| Item | Ingredients | mg/tablet | mg/capsule |
|---|---|---|---|
| | Capsule fill weight | 250 mg | 450 mg |

PROCEDURE:
(1) Mix Items 1, 2, 3 and 5 in a suitable mixer. Mill.
(2) Add talc and mix well.
(3) Encapsulate on suitable equipment.

EXAMPLE 18

TABLET FORMULATION: - (Wet Granulation)

| Item | Ingredients | mg/tablet | mg/tablet |
|---|---|---|---|
| 1. | N-(2-phenoxy-3-sulfamyl-5-carboxyphenyl)pyrrole | 0.1 | 2.0 |
| 2. | Lactose | 152.9 | 253.0 |
| 3. | Modified Starch | 25 | 55.0 |
| 4. | Pregelatinized starch | 20 | 35.0 |
| 5. | Distilled water q.s. | — | — |
| 6. | Magnesium stearate | 2 | 5 |
| | Weight of tablet | 200 mg | 350 mg |

PROCEDURE:
(1) Mix Items 1-4 in a suitable mixer.
(2) Granulate with sufficient distilled water to proper consistency. Mill.
(3) Dry in a suitable oven.
(4) Mill and mix with magnesium stearate for 3 minutes.
(5) Compress on a suitable press equipped with appropriate punches.

EXAMPLE 19

TABLET FORMULATION: (Wet -(Wet Granulation)

| Item | Ingredients | mg/tablet |
|---|---|---|
| 1. | 3(γ-hydroxybutylamino)-4-phenoxy-5-sulfamylbenzoic acid | 0.1 |
| 2. | Lactose | 152.9 |
| 3. | Modified starch | 25 |
| 4. | Pregelatinized starch | 20 |
| 5. | Distilled water q.s. | — |
| 6. | Magnesium stearate | 2 |
| | Weight of tablet | 200 mg |

PROCEDURE:
(1) Mix Items 1-4 in a suitable mixer.
(2) Granulate with sufficient distilled water to proper consistency. Mill.
(3) Dry in a suitable oven.
(4) Mill and mix with magnesium stearate for 3 minutes.
(5) Compress on a suitable press equipped with appropriate punches.

EXAMPLE 20

CAPSULE FORMULATIONS:

| Item | Ingredients | mg/capsule |
|---|---|---|
| 1. | 3(γ-hydroxybutylamino)-4-phenoxy-5-sulfamylbenzoic acid | 0.1 |
| 2. | Lactose | 203.9 |
| 3. | Starch | 30 |
| 4. | Talc | 15 |
| 5. | Aerosol OT | 1.0 |
| | Capsule fill weight | 250 mg |

PROCEDURE:
(1) Mix Items 1, 2, 3 and 5 in a suitable mixer. Mill.
(2) Add talc and mix well.
(3) Encapsulate on suitable equipment.

EXAMPLE 21

TABLET FORMULATION: - (Wet Granulation)

| Item | Ingredients | mg/tablet |
|---|---|---|
| 1. | N-(2-phenoxy-3-sulfamyl-5-carboxyphenyl)-γ-aminobutyric acid | 0.5 |
| 2. | Lactose | 186.5 |
| 3. | Modified starch | 35 |
| 4. | Pregelatinized starch | 25 |
| 5. | Distilled water q.s. | — |
| 6. | Magnesium stearate | 3 |
| | Weight of tablet | 200 mg |

PROCEDURE:
(1) Mix items 1-4 in a suitable mixer.
(2) Granulate with sufficient distilled water to proper consistency. Mill.
(3) Dry in a suitable oven.
(4) Mill and mix with magnesium stearate for 3 minutes.
(5) Compress on a suitable press equipped with appropriate punches.

I claim:
1. A compound of the formula:

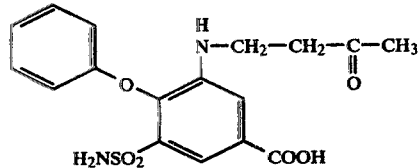

or pharmaceutically acceptable salts thereof.
2. The compound of claim 1 where said compound is 3-(γ-oxobutylamino)-4-phenoxy-5-sulfamylbenzoic acid.